United States Patent [19]

Jones et al.

[11] Patent Number: 5,175,353

[45] Date of Patent: Dec. 29, 1992

[54] 2-(2'-AMINOETHOXY)-ETHANOL SALT OF DICAMBA

[75] Inventors: Rita S. Jones, River Forest; Michael T. Chirchirillo; Johnny L. Burns, both of Chicago, all of Ill.

[73] Assignee: Sandoz Ltd., Basel, Switzerland

[21] Appl. No.: 99,279

[22] Filed: Sep. 21, 1987

Related U.S. Application Data

[63] Continuation of Ser. No. 674,628, Nov. 26, 1984, abandoned.

[51] Int. Cl.⁵ .................... C07C 713/00; C07C 65/00
[52] U.S. Cl. .................... 562/474; 564/501; 71/115
[58] Field of Search ............ 260/501.17; 562/474; 71/115; 564/508

[56] References Cited

U.S. PATENT DOCUMENTS

| | | | |
|---|---|---|---|
| 3,013,054 | 12/1961 | Richter | 260/473 |
| 3,056,669 | 10/1962 | Moyle et al. | 71/115 |
| 3,725,031 | 4/1973 | Balassa | 71/105 |

OTHER PUBLICATIONS

Wideman, Chem. Abst. 86: 43711a (1977).
Zorayan et al., Chem. Abst. 88: 52300j (1978).

*Primary Examiner*—C. Warren Ivy
*Assistant Examiner*—Raymond Covington
*Attorney, Agent, or Firm*—Gerald D. Sharkin; Richard E. Vila; Melvyn M. Kassenoff

[57] ABSTRACT

The 2-(2'-aminoethoxy)ethanol salt of dicamba is useful as a herbicidal and has the advantages of a lower volatility and excellent solubility in water and organic solvents.

1 Claim, No Drawings

2-(2'-AMINOETHOXY)-ETHANOL SALT OF DICAMBA

This is a continuation of application Ser. No. 674,628, filed Nov. 26, 1984, now abandoned.

This invention relates to a new salt of dicamba. In particular, this invention relates to the 2-(2'-aminoethoxy ethanol salt of dicamba.

Dicamba (3,6-dichloro-2-methoxybenzoic acid) has proven to be a highly beneficial herbicide. It is normally applied as the dimethylamine salt. Unfortunately, this salt has a volatility that causes the product, under certain conditions of application, to come into contact with desirable plants, such as soybeans, that it can damage. This is caused by its volatility.

It is therefore an object of the present invention to find a derivative of dicamba that will maintain or improve the beneficial properties of the product while lowering the volatility.

It is another object of the present invention to locate a compound that has the herbicidal properties of dicamba with enhanced solubility characteristics.

Other objects of the present invention will be seen from the ensuing description.

It has been found that the 2-(2'-aminoethoxy)ethanol salt of dicamba (3,6-dichloro-2-methoxybenzoic acid) decreases the volatility and improves other less advantageous properties of dicamba without detracting from its beneficial herbicidal properties.

Dicamba was described and patented in U.S. Pat. No. 3,013,054 issued Dec. 12, 1961. Since that time it has become a valuable herbicidal product, particularly in the control of weeds in corn. While it is safe to corn plants, it does not harm certain other beneficial crops, such as soybeans. Consequently, care must be taken so that it does not come into contact with such plants.

Dicamba is normally applied as the dimethylamine salt. Unfortunately, this salt is sufficiently volatile that the product applied to a corn crop can come into contact and injure adjacent crops, such as soybeans. This problem cannot be readily solved by the use of additives or other means except very careful application procedures under specified weather conditions. This is often very difficult to accomplish.

It has now been found that by using the previously unknown 2-(2'-aminoethyoxy)ethanol salt of dicamba that the product has a sufficiently low volatility, so as to prevent the product from volatilizing onto undesired valuable crops, and improved solubility without any loss of herbicidal properties. This new compound can be prepared as follows:

EXAMPLE 1

Dicamba (22.1 grams; 0.10 mole) and water (100 ml) were placed into a beaker. 2-(2'-aminoethoxy)ethanol (10.5 grams; 0.10 mole) was added to the mixture, which was stirred until the solids were dissolved. The cloudy solution was washed two times with methylene chloride, filtered, rotoevaporated and stripped under vacuum to yield the desired product, the 2-(2'-aminoethoxy)ethanol salt of dicamba (32.3 grams). It had a melting point of 76-78° C. Its elemental analysis was:

|   | Theory | Found |
|---|--------|-------|
| C | 44.19  | 43.87 |
| H | 5.25   | 5.28  |
| N | 4.29   | 4.30  |
| Cl| 21.74  | 21.09 |
| $H_2O$ | 0 | 0.74 |

In actual use, the salt is used as a solution containing four pounds of the 2-(2'-aminoethoxy)ethanol salt of dicamba per gallon of water. This is readily prepared by following the procedure of the foregoing example of mixing the dicamba, 2-(2'-aminoethoxy)ethanol and water. The necessary concentration of the salt is obtained by adding sufficient water to the solution. In order to demonstrate the herbicidal effectiveness of the new compound of this invention, a series of tests was performed in comparison with the use of the known dimethyl ammonium salt of dicamba ("DMA"). In each instance the test materials were sprayed onto the plants by standard post-emergence herbicidal test procedures. The results were as follows:

| CONTROL OF PENNSYLVANIA SMARTWEED IN CORN | | |
|---|---|---|
| COMPOUND | RATE (Pounds/Acre) | CONTROL (%) 12 Days After Application |
| Claimed Salt | 0.125 | 85 |
| " | 0.25 | 85 |
| " | 0.50 | 90 |
| " | 1.0 | 100 |
| DMA | 0.125 | 40 |
| " | 0.25 | 85 |
| " | 0.50 | 93 |
| " | 1.0 | 98 |

| CONTROL OF SMOOTH PIGWEED IN GRAIN SORGHUM | | | | |
|---|---|---|---|---|
| COMPOUND | RATE OF APPLICATION (Pounds/Acre) | CONTROL (%) Days After Application | | |
| | | 10 | 31 | 49 |
| Claimed | 0.125 | 84 | 40 | 31 |
| " | 0.25 | 98 | 92 | 84 |
| " | 0.50 | 97 | 85 | 79 |
| " | 1.0 | 98 | 84 | 86 |
| DMA | 0.125 | 73 | 0 | 0 |
| " | 0.25 | 72 | 26 | 43 |
| " | 0.50 | 88 | 60 | 71 |
| " | 1.0 | 98 | 89 | 77 |
| Control | | 0 | 0 | 0 |

| CONTROL OF SMOOTH PIGWEED IN GRAIN SORGHUM | | | |
|---|---|---|---|
| COMPOUND | RATE OF APPLICATION (Pounds/Acre) | CONTROL (%) Days After Application | |
| | | 43 | 92 |
| Claimed | 0.125 | 89 | 88 |
| " | 0.25 | 91 | 93 |
| " | 0.50 | 97 | 95 |
| " | 1.0 | 99 | 98 |
| DMA | 0.125 | 83 | 75 |
| " | 0.25 | 82 | 89 |
| " | 0.50 | 87 | 88 |
| " | 1.0 | 94 | 94 |
| Control | | 0 | 0 |

CONTROL OF REDROOT PIGWEED IN GRAIN SORGHUM

| COMPOUND | RATE OF APPLICATION (Pounds/Acre) | CONTROL (%) Days After Application 7 | 51 |
|---|---|---|---|
| Claimed | 0.125 | 70 | 99 |
| " | 0.25 | 90 | 98 |
| " | 0.50 | 87 | 96 |
| " | 1.0 | 90 | 99 |
| DMA | 0.125 | 57 | 91 |
| " | 0.25 | 80 | 99 |
| " | 0.50 | 83 | 96 |
| " | 1.0 | 90 | 99 |
| Control | | 0 | 0 |

In order to demonstrate the reduced volatility of the 2-(2-aminoethoxy)ethanol salt of dicamba in comparison to the volatility of the commercial dimethylamine salt of dicamba, experiments were performed on these compounds.

EXAMPLE 6

Dimethylamine salt of $14_C$-dicamba ("DMA") and 2-(2-aminoethoxy)ethanol salt of $14_C$-dicamba were prepared. The materials were applied to glass petri dishes at a rate of about one pound per acre and maintained at 30° C. and 70% to 90% relative humidity. Samples were taken at 0, 2, 5, 15 and 30 days to determine the amounts of radiocarbon remaining on the petri dishes, as follows:

| DAYS: | 0 | 2 | 7 | 15 | 30 | Half Life (Days) |
|---|---|---|---|---|---|---|
| Claimed | 99.42 | 99.25 | 97.63 | 100.71 | 97.01 | 1257 |
| Compound (%) DMA (%) | 91.52 | 87.16 | 90.35 | 90.42 | 79.86 | 180 |

The chemical stability of the 2-(2-aminoethoxy)ethanol salt of dicamba was determined at 122°F. with the following results:

| TIME (Days) | DICAMBA (%) |
|---|---|
| 0 | 39.6 |
| 7 | 40.1 |
| 14 | 39.9 |
| 28 | 39.5 |
| 56 | 39.4 |
| 84 | 39.5 |

It can be seen that the compound of the present invention has a lower volatility than the previously used salts of dicamba, excellent chemical stability and herbicidal utility.

In addition, the 2-(2'-aminoethoxy)ethanol salt of dicamba is unique in having a high solubility in water. In fact, solution containing six pounds of the salt per gallon of water are readily prepared. This permits the ready preparation of high concentration solutions without the need for additives or solvents.

Also, the 2-(2-aminoethoxy)ethanol salt of dicamba is readily soluble in organic solvents such as Butyl Cellosolved, 2-ethyl-1-hexanol and cyclohexanone. This permits the formulation of emulsifiable concentrates containing up to four pounds of the salt per gallon of solvent.

Of equal value is the fact that the salt of this invention has no odor.

We claim:

1. The 2-(2-aminoethoxy)ethanol salt of 3,6-dichloro-2-methoxybenzoic acid.

* * * * *

UNITED STATES PATENT AND TRADEMARK OFFICE
CERTIFICATE OF CORRECTION

PATENT NO. : 5,175,353
DATED : December 29, 1992
INVENTOR(S) : Rita S. Jones, Michael T. Chirchirillo and Johnny L. Burns It is certified that error appears in the above-identified patent and that said Letters Patent is hereby corrected as shown below:

Abstract, line 2, "herbicidal" should read -- herbicide --. Column 1, lines 8-9, "aminoethoxy ethanol" should read -- aminoethoxy)ethanol --; line 36, "does not" should read -- does --; and line 47, "aminoethyoxy)ethanol" should read -- aminoethoxy)ethanol --. Column 2, line 19, "dimethyl ammonium" should read -- dimethylammonium --; -- EXAMPLE 2 -- should be inserted on line 23; -- EXAMPLE 3 -- should be inserted on line 37; and -- EXAMPLE 4 -- should be inserted on line 53. Column 3, -- EXAMPLE 5 -- should be inserted on line 1. Column 4, line 31, "2-(2-" should read -- 2-(2'- --; lines 32-33, "Cellosolved," should read -- Cellosolve®, --; and line 40, "2-(2-" should read -- 2-(2'- --.

Signed and Sealed this

Twenty-second Day of March, 1994

BRUCE LEHMAN

Attest:

Attesting Officer    Commissioner of Patents and Trademarks